United States Patent [19]

Noveroske et al.

[11] Patent Number: 5,498,773
[45] Date of Patent: Mar. 12, 1996

[54] HERBICIDAL COMPOSITIONS WITH INCREASED CROP SAFETY

[75] Inventors: Robert L. Noveroske, Indianapolis; Ronald W. McCormick, Noblesville, both of Ind.

[73] Assignee: DowElanco, Indianapolis, Ind.

[21] Appl. No.: 220,138

[22] Filed: Mar. 30, 1994

Related U.S. Application Data

[63] Continuation-in-part of Ser. No. 976,113, Nov. 13, 1992, abandoned, which is a continuation of Ser. No. 695,195, May 3, 1991, abandoned.

[51] Int. Cl.⁶ .................................................. A01N 25/32
[52] U.S. Cl. .................................. 504/103; 504/110
[58] Field of Search ................................ 504/103, 124, 504/241, 242, 110

[56] References Cited

U.S. PATENT DOCUMENTS

| | | | |
|---|---|---|---|
| 3,131,509 | 5/1964 | Hoffmann | 47/1 |
| 4,127,405 | 11/1978 | Levitt | 71/93 |
| 4,547,215 | 10/1985 | Wolf | 71/92 |
| 4,818,273 | 4/1989 | Kleschick et al. | 71/90 |
| 4,840,663 | 6/1989 | Quadranti et al. | 71/93 |
| 4,936,900 | 6/1990 | Hyson | 71/90 |
| 4,954,163 | 9/1990 | Kleschick et al. | 71/92 |
| 5,236,887 | 8/1993 | Noveroske | 504/105 |

FOREIGN PATENT DOCUMENTS 59-10501  1/1984  Japan.

OTHER PUBLICATIONS

1987 Farm Chemicals Handbook, Meister Publishing Co., Willoughby, Ohio, pp. B51–B52, 1987.

*Primary Examiner*—S. Mark Clardy
*Assistant Examiner*—Brian Bembenick
*Attorney, Agent, or Firm*—S. Preston Jones; Kenneth L. Loertscher; D. Wendell Osborne

[57] ABSTRACT

Disclosed are herbicidal concentrate formulation compositions having reduced grass crop plant phytotoxicity comprising certain sulfonamide or sulfonylurea herbicides in admixture with a non-herbicidal organic or inorganic acid or mixture thereof in an amount sufficient to insure that during the post-emergent agricultural uses thereof in water diluted form the pH of the mixture is below about 5; also disclosed is the preparation of said compositions, aqueous formulations of said concentrate and the use of said formulations.

84 Claims, No Drawings

5,498,773

HERBICIDAL COMPOSITIONS WITH INCREASED CROP SAFETY

CROSS-REFERENCE TO RELATED APPLICATIONS

This application is a continuation-in-part of application Ser. No. 07/976,113, filed Nov. 13, 1992 abandoned, which in turn is a continuation of application Ser. No. 07/695,195, filed May 3, 1991, now abandoned.

FIELD OF THE INVENTION

The present invention is directed to herbicidal concentrate formulation compositions comprising certain sulfonamide or sulfonylurea herbicides in admixture with a non-herbicidal organic or inorganic acid or mixture thereof in an amount sufficient to insure that during post-emergent agricultural uses thereof in water diluted form, the pH of the mixture is below about 5, the preparation of said concentrates and the aqueous formulations thereof and the use of said formulations are also a part of the present invention.

BACKGROUND OF THE INVENTION

Various herbicides, such as, for example, those of the sulfonamide and sulfonylurea classes are known to be active as selective pre- and post-emergent weed control agents. Many times when certain of these compounds are employed for post-emergent uses at the dosage rates usually necessary for the control of many of the broadleaf and/or grassy weeds, serious loss of some sensitive broadleaf and/or grassy crop plants occur.

One procedure to overcome the above-indicated sensitivity responses of plants to the various herbicidal compounds involves varying the dosage rate. When a reduction in the dosage rate is used to avoid phytotoxicity to the crop plants, reduced weed control is often the result.

Another procedure involves changing the time of application or modifying the ingredients used in the formulations containing the active compound. Other known procedures include treatment of the seeds of the crop plants with an agent antagonistic to the herbicide prior to planting as described in U.S. Pat. No. 3,131,509.

It has now been found that the post-emergent phytotoxicity of certain sulfonamide and sulfonylurea herbicides towards grass crop plants is reduced by admixing said herbicides with a non-herbicidal organic or inorganic acid or mixtures thereof in an amount sufficient to reduce the pH of the water diluted form of the herbicide/acid mixture to below about 5.

DESCRIPTION OF KNOWN PRIOR ART

U.S. Pat. No. 4,127,405 is directed to certain sulfonamides and their use as selective herbicides. It is further indicated that the claimed compounds can be used in combination with other herbicides including some which are herbicidal acids. It is noted that no pH of the herbicide formulation is set forth.

U.S. Pat. No. 4,547,215 is directed to certain sulfonamides and their use as selective pre- or post-emergent herbicides. It is further indicated that the claimed compounds can be used in combination with other herbicides and list about 70 different herbicides including some which are herbicidal acids. It is noted that no pH of the herbicide formulation is set forth.

U.S. Pat. No. 4,840,663 teach the control of weeds in rice by the use of a synergistic mixture of N-(2-(2-metoxyethoxy)phenylsulfonyl)-N' -(4,6-dimethoxy-1,3,5-trazin-2-yl)urea and a herbicidal compound selected from a large grouping of different types of herbicides including three which are herbicidal acids. It is noted that no pH of the herbicide formulation is set forth.

U.S. Pat. No. 4,936,900 is directed to stabilized compositions having a pH of 6–10 and containing a mixture of a sulfonylurea or one of its agriculturally suitable salts with a salt or mixture of salts of a carboxylic or inorganic acid. It is further indicated that other herbicides may be added to the mixture and a very large list of other herbicides is set forth including some which are herbicidal acids.

SUMMARY OF THE INVENTION

The present invention is directed to herbicidal concentrate compositions containing certain sulfonamide or sulfonylurea herbicides in admixture with a non-herbicidal organic or inorganic acid or mixture thereof. The invention is also directed to the preparation of said concentrates, aqueous formulations thereof having a pH of below about 5 prepared from said concentrates and the agricultural uses of the thus prepared aqueous formulations by applying herbicidally effective amounts of said formulations to plants or their habitat in the post-emergent kill and control of the weeds present in many broadleaf and grass crops.

DESCRIPTION OF SOME PREFERRED EMBODIMENTS

The compositions of the present invention have been found to possess desirable herbicidal activity for use in the post-emergent control of many broadleaf weeds such as velvetleaf, lambsquarter, kochia, pigweed, cocklebur, and buckwheat while showing high selectivity to important broadleaf crops, such as legumes, for example, soybeans and other such crops and grass crops such as wheat, barley, sorghum, rice and corn. While all of the listed herbicides are useful to control weeds some of the compounds are more selective towards broadleaf crops than grass crops and others are more selective towards grass crops than broadleaf crops.

The sulfonamide and sulfonylurea herbicides useful in the practice of the present invention are the compounds:
Ally (Metsulfuron-methyl):
  methyl 2-((4-methoxy-6-methyl-1,3,5 -trizian-2-yl)-ureidosulfonyl)benzoate;
Classic: (Chlorimuron-ethyl:
  ethyl 2-(((((4-chloro-6-methoxypyrimidin-2-yl)amino)carbonyl)amino)sulfonyl)benzoate;
Express/Granstar (Tribenuron-methyl):
  methyl 2-(((((4-methoxy-6-methyl-1,3,5-trizian-2yl)methylamino)carbonyl)amino)sulfonyl)benzoate;
Glean (Chlorsulfuron):
  1-(2-chlorophenylsulfonyl)-3-(4-methoxy-6-methyl-1,3,5-triazin-2-yl)urea;
Harmony (Thifensulfuron):
  3-((((N-(4-methoxy-6-methyl-1,3,5-triazin-2-yl)amino)carbonyl)amino)sulfonyl)-2-thiophenecarboxylic acid;
N-(2,6-dichloro-3-methylphenyl)-5,7-dimethoxy-1,2,4-triazolo[1,5-a]pyrimidine-2 -sulfonamide;
N-(2,6-difluorophenyl)-5-methyl-1,2,4-triazolo-(1,5-c)pyrimidine-2-sulfonamide;
N-(2,6-dichlorophenyl)-5-ethoxy-7-fluoro-1,2,4-triazolo-(1, 5-c)pyrimidine-2-sulfonamide;

2-(((7-fluoro-5-ethoxy-1,2,4-triazolo(1,5-c)pyrimidin- 2-yl) sulfonyl)amino)-3-fluorobenzoic acid, methyl ester;

N-(2,6-difluorophenyl)-8-chloro 5-methoxy-1,2,4-triazolo-(1,5-c)pyrimidine-2-sulfonamide;

N-(2,6-difluorophenyl)-5-methoxy-8-fluoro-1,2,4-triazolo-(1,5-c)pyrimidine-2sulfonamide, and N-(2-chloro-6-fluorophenyl)-5-ethoxy-7-fluoro-1,2,4-triazolo-(1,5-c)pyrimidine-2-sulfonamide;

Non-herbicidal acids which are useful in preparing the aqueous formulations of the present invention are those which are capable of reducing the pH of the aqueous formulation to below about 5 and are not reactive with or otherwise detrimental to the activity of the sulfonamide or sulfonylurea herbicides. Representative acids include, for example:

| | |
|---|---|
| acetic acid; | nitric acid; |
| citric acid; | nitrous acid; |
| dodecylbenzenesulfonic acid; | oxalic acid; |
| glycolic acid; | phosphoric acid; |
| hydrochloric acid; | phthalic acid; |
| lactic acid; | pyrophosphoric acid; |
| maleic acid; | sulfuric acid; and |
| malonic acid; | tartaric acid. |
| monoammonium hydrogen phosphate (($NH_4$)$H_2PO_4$) | |

Herbicidal acids are not normally used to reduce the pH of the present formulations. These herbicidal acids are most frequently used commercially in the salt or ester form and as such, they do not appreciably alter the pH. Since each of the herbicidal acids differ in acid strength, the amounts required to adjust the pH to below about 5 would vary considerably. The acid could be present in an amount of from two to ten or more times the label amount required for use as herbicides having parallel crop selectivity to the sulfonamide or sulfonylurea herbicides of the present invention. For example, the crop plant selectively of the combination of the active sulfonamide or sulfonylurea herbicides and the excess amount of the active acid herbicide could lead to undesirable plant responses whereby crop selectivity could be upset. While an additional crop selective active acid herbicide could augment the activity of the sulfonamide or sulfonylurea when it is employed at the label rate; at a higher rate it can become quite antagonistic.

The herbicidally effective amount of the active sulfonamide or sulfonylurea herbicide in the concentrate composition generally is from about 0.5 to about 90 percent by weight or more. Concentrations from about 2 to about 50 percent by weight are often preferred. The amount of said herbicide present in the final treating composition (mixture) is usually sufficient to provide during post-emergent control of broadleafed weeds from about 1.0 to about 70.0 grams of the said active material per hectare, preferably from about 2.0 to about 35 grams of the said active material per hectare; for pre-emergent control of broadleafed weeds, the active herbicide is provided in an amount of about 10 to about 200 g ai/hectare.

The amount of non-herbicidal acid present in the concentrate composition is generally from about 0.5 to about 80 percent by weight or more. The amount of acid present in the final treating composition (mixture) is sufficient to maintain the pH of the mixture below about 5.0 and usually from about pH 4.0 to about 2.5; and is usually present in an amount sufficient to provide during application, from about 15 to about 1200 grams of acid equivalent per hectare.

It is frequently desirable to incorporate a surface active agent in the composition of the present invention. Such surface active or wetting agents can be anionic, cationic or nonionic in character. A suitable list for reference may be found in "MeCuteheon's Emulsifiers and Detergents" (1981 Edition).

Examples of anionic surfactants are the calcium and amine salts of dodecylbenzenesulfonic acid and sodium diisooctylsulfosuccinate.

Examples of nonionic surfactants are the condensation products of fatty acid esters, fatty alcohols, fatty acid amides or fatty amines with ethylene and/or propylene oxide, alkyl, alkenyl, or polyaryl-substituted phenols with ethylene and/or propylene oxide, fatty esters of polyhydric alcohol ethers, e.g., sorbitan fatty acid esters, condensation products of such esters with ethylene oxide, e.g., polyoxyethylene sorbitan fatty acid esters, block copolymers of ethylene oxide and propylene oxide, ethoxylated lanolin alcohols or ethoxylated lanolin acids.

Representative of the above surface active or wetting agents useful in the practice of the present invention include products such as, for example:

PG 26-2: a secondary butyl(((phenoxy(polypropylene)oxy)polyethylene)oxy) ethanol(5 moles EO,4 moles PO) a product of The Dow Chemical Co.

Triton (Ortho) X-77: alkylarylpolyoxyethylene glycol, a product of Chevron Chemical Co.

Silwet L-77: nonionic silicone glycol copolymer; a product of Union Carbide Corp.

Examples of a cationic agent include, for instance, an aliphatic mono-, di- or polyamine as an acetate or oleate.

Anionic/nonionic blends are preferred and are often advantageously chosen as pre-blended systems for ease of handling, reproducibility and cost effectiveness.

The choice of suitable surfactants are well within the capabilities of one skilled in the art.

The amount of surfactant present in the concentrate composition will generally be in the range of from about 0.0 percent to about 10 percent, preferably from 1.0 percent to 7.0 percent by weight. The amount of surfactant present in the final treating composition (mixture) is usually from about 0.0 to about 5.0 percent by weight, preferably from 0.0 percent to 0.5 percent by weight.

The exact amount of the composition to be applied is dependent not only on the specific active ingredient contained therein, but also on the particular action desired, the plant species to be controlled, the stage of growth thereof as well as the specific part of the plant to be contacted.

The exact herbicidally effective amount of the composition to be applied is also dependent not only on the specific active ingredient contained therein, but also on the particular action desired, the plant species to be controlled, the stage of growth thereof as well as the specific part of the plant to be contacted or type of growth medium in which the seeds are planted.

The following examples illustrate the present invention and the manner by which it can be practiced but, as such, should not be construed as limitations upon the overall scope of the same. In addition, the pH value given is taken from the run with the highest acid concentration and the pH of all runs is less than 5.0.

EXAMPLE I

Representative compositions of the present invention were evaluated to determine their phytotoxicity effect in post-emergent operations on corn plants.

Aqueous dispersions were prepared by admixing a predetermined amount of one of the compounds N-(2,6-dichlorophenyl)- 5-ethoxy-7-fluoro-1,2,4-triazolo-(1,5-c)pyrimidine-2-sulfonamide (Compound A), 2-(((7-flouro-5-ethoxy-1,2,4-triazolo(1,5-c)pyrimidin-2-yl)sulfonyl)amino)-3-fluorobenzoic acid: methyl ester (Compound B), Metsulfuron-methyl (Compound C) or Thifensulfuron (Compound D) with a predetermined quantity of water, a predetermined amount of phosphoric acid ($H_3PO_4$) to adjust the pH to the hereinafter set forth value and a predetermined amount of the surfactant X-77 to give aqueous dispersions containing predetermined amount of one of the compounds, as the sole toxicant.

Corn seeds were planted in beds of good agricultural peat based soil and grown in a greenhouse. After the plants had emerged and had grown to a height of about 4 inches, separate beds of the plants were sprayed with one of the above-prepared compositions at predetermined treating rates in grams of the active ingredient per hectare (g ai/ha). Other beds were treated only with a water-surfactant mixture (control), containing no active compound, and others containing the active compound and surfactant, but no acid, to serve as controls. After treatment, the beds were maintained for about one week under greenhouse conditions conducive for good plant growth. At the end of this period, the beds were examined to determine the percentage of phytotoxicity to the corn plants. The results of these examinations are set forth below in Table I.

TABLE I

| Test mixture | pH | % growth reduction as a % of control at indicated g ai/ha** | | |
|---|---|---|---|---|
| | | 17.5 | 8.8 | 4.4 |
| Compound A/NA | 6.59 | 40.0 | 35.0 | 30.0 |
| Compound A + $H_3PO_4$ | 3.01 | 30.0 | 25.0 | 25.0 |
| Compound B/NA | 6.68 | 15.0 | 17.5 | 20.0 |
| Compound B + $H_3PO_4$ | 3.01 | 0.0 | 0.0 | 0.0 |
| Compound C/NA | 7.44 | NT | 45.0 | 45.0 |
| Compound C + $H_3PO_4$ | 3.01 | NT | 40.0 | 40.0 |
| Compound D/NA | 7.45 | 35.0 | 25.0 | 15.0 |
| Compound D + $H_3PO_4$ | 3.00 | 25.0 | *** | 10.0 |
| control | 7.33 | 0.0 | 0.0 | 0.0 |

NA = no acid control
* = not tested
** = grams of active ingredient per hectare.
*** = not understood spike in crop kill.

EXAMPLE II

Representative compositions of the present invention were evaluated to determine their phytotoxicity effect in post-emergent operations on soybean plants.

Aqueous dispersions were prepared by admixing a predetermined amount of one of the compounds N-(2,6-dichlorophenyl)- 5-ethoxy-7-fluoro-1,2,4-triazolo-(1,5-c)pyrimidine-2-sulfonamide (Compound A), 2-(((7-fluoro-5-ethoxy-1,2,4-triazolo(1,5-c)pyrimidin-2-yl)-sulfonyl)amino)-3-fluorobenzoic acid: methyl ester (Compound B), Thifensulfuron (Compound D) or N-(2-chloro-6-fluorophenyl)-5-ethoxy-7-fluoro-1,2,4-triazolo-(1,5-c)pyrimidine-2-sulfonamide (Compound E) with a predetermined quantity of water, a predetermined amount of phosphoric acid ($H_3PO_4$) to adjust the pH to the hereinafter set forth value and a predetermined amount of the surfactant X-77 to give aqueous dispersions containing predetermined amount of one of the compounds, as the sole toxicant.

Soybean seeds were planted in beds of good agricultural peat based soil and grown in a greenhouse. After the plants had emerged and had grown to a height of about 8 inches, separate beds of the plants were sprayed with one of the above-prepared compositions at a predetermined treating rate in grams of the active ingredient per hectare (g ai/ha). Other beds were treated only with a water-surfactant mixture (control), containing no active compound, and others containing the active compound and surfactant, but no acid, to serve as controls. After treatment, the beds were maintained for about one week under greenhouse conditions conducive for good plant growth. At the end of this period after treatment, the beds were examined to determine the percentage of phytotoxicity to the soybean plants. The results of these examinations are set forth below in Table II.

TABLE II

| Test mixture | pH | % growth reduction as a % of control at indicated g ai/ha** | | |
|---|---|---|---|---|
| | | 17.5 | 8.8 | 4.4 |
| Compound A/NA | 6.59 | 15.0 | 15.0 | 15.0 |
| Compound A + $H_3PO_4$ | 3.01 | 0.0 | 0.0 | 0.0 |
| Compound B/NA | 6.68 | 10.0 | 10.0 | 10.0 |
| Compound B + $H_3PO_4$ | 3.01 | 0.0 | 0.0 | 0.0 |
| Compound D/NA | 7.45 | 50.0 | 50.0 | 50.0 |
| Compound D + $H_3PO_4$ | 3.00 | 35.0 | 35.0 | 35.0 |
| Compound E/NA | 6.62 | 35.0 | 35.0 | 20.0 |
| Compound E + $H_3PO_4$ | 3.00 | 15.0 | 15.0 | 15.0 |
| control | 7.33 | 0.0 | 0.0 | 0.0 |

NA = no acid control
** = grams of active ingredient per hectare.

EXAMPLE III

Representative compositions of the present invention were evaluated to determine their phytotoxicity effect in post-emergent operations on corn plants.

Aqueous dispersions were prepared by admixing a predetermined amount of one of Compound A, Compound B and N-(2,6-difluorophenyl)-5-methyl-1,2,4-triazolo-(1,5-a)pyramibine)-2-sulfonamide (Compound F), both Compounds A and B as as defined hereinbefore, with a predetermined quantity of water, a predetermined amount of phosphoric acid ($H_3PO_4$) to adjust the pH to the hereinafter set forth value and a predetermined amount of the surfactant X-77 to give aqueous dispersions containing predetermined amount of one of the compounds, as the sole toxicant.

Seeds of the crop plants corn and soybean and the weed species velvetleaf, cocklebur and pigweed were planted in beds of good agricultural growth medium and grown in a greenhouse. After the plants had emerged and had grown to a height of about 1–8 inches, depending on the plant species, separate beds of the plants were sprayed with one of the above-prepared compositions at a predetermined treating rate in grams of the active ingredient per hectare (g ai/ha). Other beds were treated only with a water-surfactant mixture, containing no active compound; and others containing the active compound and surfactant, but no acid, to serve as controls. After treatment, the beds were maintained under greenhouse conditions conducive for good plant growth for about seventeen days for corn and soybean and 20 days for the velvetleaf, cocklebur and pigweed plants. At the end of this period, the beds were examined to determine the percentage of phytotoxicity to the crop plants and the kill and control of the weeds. The results of these examinations are set forth below in Table III.

TABLE III

| Test mixture | pH | Corn 17.5 | 4.4 | 1.1 | Soybean 17.5 | 4.4 | 1.1 | VL[a] 17.5 g ai/ha | CB[a] 17.5 g ai/ha |
|---|---|---|---|---|---|---|---|---|---|
| Compound A/NA | 7.74 | 50.0 | 20.0 | 10.0 | | | | 100.0 | 100.0 |
| Compound A + $H_3PO_4$ | 3.19 | 15.0 | 0.0 | 0.0 | | | | 97.5 | 100.0 |
| Compound B/NA | 7.76 | 10.0 | 0.0 | 0.0 | | | | — | 100.0 |
| Compound B + $H_3PO_4$ | 3.18 | 5.0 | 0.0 | 0.0 | | | | — | 100.0 |
| Compound F/NA | 7.44 | 15.0 | 0.0 | 0.0 | 15.0 | 10.0 | 5.0 | 95.0 | — |
| Compound F + $H_3PO_4$ | 3.13 | 10.0 | 0.0 | 0.0 | 5.0 | 0.0 | 0.0 | 95.0 | — |
| control | 7.75 | 0.0 | | | 0.0 | | | 0.0 | 0.0 |

% growth reduction as a % of control at indicated g ai/ha**

NA = no acid control
** = grams of active ingredient per hectare.

EXAMPLE IV

Representative compositions of the present invention were evaluated to determine their phytotoxicity effect in post-emergent operations on soybean plants.

Aqueous dispersions were prepared by admixing a predetermined amount of N-(2,6-difluorophenyl)-5-methyl-1,2,4-triazolo(1,5-a)pyrimidine-2-sulfonamide with a predetermined quantity of water, a predetermined amount of monoammonium hydrogen phosphate ($NH_4H_2PO_4$) to adjust the pH to the hereinafter set forth value and a predetermined amount of the surfactant X-77 to give aqueous dispersions containing predetermined amount of the compound, as the sole toxicant.

Soybean seeds and seeds of the weed species lambsquarter (LQ) and cocklebur (CB) were planted in beds of good agricultural peat based soil and grown in a greenhouse. After the plants had emerged and had grown to a height of about 1–8 inches, depending on the plant species, separate beds of the plants were sprayed with one of the above-prepared compositions at a predetermined treating rate in grams of the active ingredient per hectare (g ai/ha). Other beds were treated only with a water-surfactant mixture, containing no active compound, and others containing the active compound and surfactant, but no acid, to serve as controls. After treatment, the beds were maintained for about seven days under greenhouse conditions conducive for good plant growth. At the end of this period, the beds were examined to determine the percentage of phytotoxicity to the soybean plants. The results of these examinations are set forth below in Table IV.

TABLE IV

| Test mixture | pH | soybean | LQ* | CB* |
|---|---|---|---|---|
| Compound/NA | 8.9 | 10.0 | 95.0 | 100.0 |
| Compound + $NH_4H_2PO_4$ | 5.0 | 5.0 | 95.0 | 95.0 |

% growth reduction as a % of control at indicated 17.5 g ai/ha**

NA = no acid control
* = graded 17 days after treatment
** = grams of active ingredient per hectare.

TABLE IV

EXAMPLE V

Representative compositions of the present invention were evaluated to determine their phytotoxicity effect in post-emergent operations on wheat plants.

Aqueous dispersions were prepared by admixing a predetermined amount of N-(2,6-dichloro-3-methylphenyl)-5,7-dimethoxy-1,2,4-triazolo[1,5a]pyrimidine-2-sulfonamide with a predetermined quantity of water, a predetermined amount of monoammonium hydrogen phosphate to adjust the pH to the hereinafter set forth value and a predetermined amount of the surfactant X-77 to give aqueous dispersions containing predetermined amount of the compound, as the sole toxicant.

Wheat seeds were planted in beds of good agricultural peat based soil and grown in a greenhouse. After the plants had emerged and had grown to a height of about 4 inches, separate beds of the plants were sprayed with one of the above-prepared compositions at a predetermined treating rate in grams of the active ingredient per hectare (g ai/ha). Other beds were treated only with a water-surfactant mixture (control), containing no active compound, and others containing the active compound and surfactant, but no acid, to serve as controls. After treatment, the beds were maintained for about one week under greenhouse conditions conducive for good plant growth. At the end of this period, the beds were examined to determine the percentage of phytotoxicity to the wheat plants. The results of these examinations are set forth below in Table V.

TABLE V

| Test mixture | pH | 17.5 | 8.8 | 4.4 |
|---|---|---|---|---|
| Compound/NA | 7.8 | 12.5 | 7.5 | 0.0 |
| Compound + $H_3PO_4$ | 5.0 | 0.0 | 0.0 | 0.0 |
| Compound + $H_3PO_4$ | 3.0 | 0.0 | 0.0 | 0.0 |
| control | 8.74 | 0.0 | 0.0 | 0.0 |

% growth reduction as a % of control at indicated g ai/ha**

NA = no acid control
** = grams of active ingredient per hectare.

What is claimed is:

1. A herbicidal formulation concentrate composition comprising, as the active material, a herbicidally effective amount of from about 0.5 to about 90 percent by weight of a sulfonamide or sulfonylurea herbicide from the group consisting of Chlorimuron-ethyl,
Chlorsulfuron,
Metsulfuron-methyl,
Tribenuron-methyl, Thifensulfuron,
N-(2,6-dichloro-3-methylphenyl)-B,7-dimethoxy-1,2,4-triazolo(1,5-a)pyrimidine-2-sulfonamide,
N-(2,6-dichlorophenyl)-5-ethoxy-7-fluoro-1,2,4-triazolo-(1,5-c)pyrimidine-2-sulfonamide,
N-(2-chloro-6-fluorophenyl)-5-ethoxy-7-fluoro-1,2,4-triazolo-(1,5-c)pyrimidine-2-sulfonamide,
N-(2,6-difluorophenyl)-8-chloro 5-methoxy-1,2,4-triazolo-(1,5-c)pyrimidine-2-sulfonamide,
N-(2,6-difluorophenyl)-5-methyl-1,2,4-triazolo-(1,5-a)pyrimidine-2-sulfonamide,
N-(2,6-difluorophenyl)-5-methoxy-8-fluoro-1,2,4-triazolo-(1,5-c)pyrimidine-2-sulfonamide, and
2-(((7-fluoro-5-ethoxy-1,2,4-triazolo(1,5-c)pyrimidin-2-yl)sulfonyl)amino)-3-fluorobenzoic acid, methyl ester,
or mixtures of said compounds, in admixture with from about 0.5 to about 80 percent of said concentrate of a non-herbicidal acidic material from the group consisting of non-herbicidal organic or inorganic acids or the non-herbicidal acid salts of said inorganic acids or mixtures thereof, said acidic material being present in an amount sufficient to insure that during post-emergent agricultural uses of said formulation in water diluted form, the pH of the water diluted mixture is below about 5.

2. A composition as defined in claim 1 wherein the active compound is Chlorimuron-ethyl.

3. A composition as defined in claim 2 wherein the acid is phosphoric acid.

4. A composition as defined in claim 2 wherein the acid is monoammonium hydrogen phosphate.

5. A composition as defined in claim 1 wherein the active compound is Chlorsulfuron.

6. A composition as defined in claim 5 wherein the acid is phosphoric acid.

7. A composition as defined in claim 5 wherein the acid is monoammonium hydrogen phosphate.

8. A composition as defined in claim 1 wherein the active compound is Metsulfuron-methyl.

9. A composition as defined in claim 8 wherein the acid is phosphoric acid.

10. A composition as defined in claim 8 wherein the acid is monoammonium hydrogen phosphate.

11. A composition as defined in claim 1 wherein the active compound is Tribenuron-methyl.

12. A composition as defined in claim 11 wherein the acid is phosphoric acid.

13. A composition as defined in claim 11 wherein the acid is monoammonium hydrogen phosphate.

14. A composition as defined in claim 1 wherein the active compound is Thifensulfuron.

15. A composition as defined in claim 14 wherein the acid is phosphoric acid.

16. A composition as defined in claim 14 wherein the acid is monoammonium hydrogen phosphate.

17. A composition as defined in claim 1 wherein the active compound is N-(2,6-dichloro-3-methylphenyl)-5,7-dimethoxy-1,2,4-triazolo-(1,5-a)pyrimidine-2-sulfonamide.

18. A composition as defined in claim 17 wherein the acid is phosphoric acid.

19. A composition as defined in claim 17 wherein the acid is monoammonium hydrogen phosphate.

20. A composition as defined in claim 1 wherein the active compound is N-(2,6-dichlorophenyl)-5-ethoxy-7-flouro-1,2,4-triazolo-(1,5-c)pyrimidine-2-sulfonamide.

21. A composition as defined in claim 20 wherein the acid is phosphoric acid.

22. A composition as defined in claim 20 wherein the acid is monoammonium hydrogen phosphate.

23. A composition as defined in claim 1 wherein the active compound is N-(2-chloro-6-flourophenyl)-5-ethoxy-7-fluoro-1,2,4-triazolo-(1,5-c)pyrimidine-2-sulfonamide.

24. A composition as defined in claim 23 wherein the acid is phosphoric acid.

25. A composition as defined in claim 23 wherein the acid is monoammonium hydrogen phosphate.

26. A composition as defined in claim 1 wherein the active compound is N-(2,6-difluorophenyl)-8-chloro-5-methoxy-1,2,4-triazolo-(1,5-c)pyrimidine-2-sulfonamide.

27. A composition as defined in claim 26 wherein the acid is phosphoric acid.

28. A composition as defined in claim 26 wherein the acid is monoammonium hydrogen phosphate.

29. An aqueous herbicidal formulation composition comprising, as the active material, a herbicidally effective amount of a sulfonamide or sulfonylurea herbicide from the group consisting of
Chlorimuron-ethyl,
Chlorsulfuron,
Metsulfuron-methyl,
Tribenuron-methyl,
Thifensulfuron,
N-(2,6-dichloro-3-methylphenyl)-5,7-dimethoxy-1,2,4-triazolo(1,5-a)pyrimidine-2-sulfonamide,
N-(2,6-dichlorophenyl)-5-ethoxy-7-fluoro-1,2,4-triazolo-(1,5-c)pyrimidine-2-sulfonamide,
N-(2-chloro-6-fluorophenyl)-5-ethoxy-7-fluoro-1,2,4-triazolo-(1,5-c)pyrimidine-2-sulfonamide,
N-(2,6-difluorophenyl)-8-chloro-5-methoxy-1,2,4-triazolo-(1,5-c)pyrimidine-2-sulfonamide,
N-(2,6-difluorophenyl)-5-methyl-1,2,4-triazolo-(1,5-a)pyrimidine-2-sulfonamide,
N-(2,6-difluorophenyl)-5-methoxy-8-fluoro-1,2,4-triazolo-(1,5-c)pyrimidine-2-sulfonamide, and
2-(((7-fluoro-5-ethoxy-1,2,4-triazolo(1,5-c )pyrimidin-2-yl)sulfonyl)amino)-3-fluorobenzoic acid, methyl ester,
or mixtures of said compounds, in admixture with an amount of a non-herbicidal acidic material from the group consisting of non-herbicidal organic or inorganic acids or the acid salts of said non-herbicidal inorganic acids or mixtures thereof sufficient to reduce the pH of the aqueous formulation to below about 5 and to provide in the final treating formulation from about 15 to about 1200 grams of acid equivalent per hectare.

30. A composition as defined in claim 29 wherein the active compound is Chlorimuron-ethyl.

31. A composition as defined in claim 30 wherein the acid is phosphoric acid.

32. A composition as defined in claim 30 wherein the acid is monoammonium hydrogen phosphate.

33. A composition as defined in claim 29 wherein the active compound is Chlorsulfuron.

34. A composition as defined in claim 33 wherein the acid is phosphoric acid.

35. A composition as defined in claim 33 wherein the acid is monoammonium hydrogen phosphate.

36. A composition as defined in claim 29 wherein the active compound is Metsulfuron-methyl.

37. A composition as defined in claim 36 wherein the acid is phosphoric acid.

38. A composition as defined in claim 36 wherein the acid is monoammonium hydrogen phosphate.

39. A composition as defined in claim 29 wherein the active compound is Tribenuron-methyl.

40. A composition as defined in claim 39 wherein the acid is phosphoric acid.

41. A composition as defined in claim 39 wherein the acid is monoammonium hydrogen phosphate.

42. A composition as defined in claim 29 wherein the active compound is Thifensulfuron.

43. A composition as defined in claim 42 wherein the acid is phosphoric acid.

44. A composition as defined in claim 42 wherein the acid is monoammonium hydrogen phosphate.

45. A composition as defined in claim 29 wherein the active compound is N-(2,6-dichloro-3-methylphenyl)-5,7-dimethoxy-1,2,4-triazolo-(1,5-a)pyrimidine-2-sulfonamide.

46. A composition as defined in claim 45 wherein the acid is phosphoric acid.

47. A composition as defined in claim 45 wherein the acid is monoammonium hydrogen phosphate.

48. A composition as defined in claim 29 wherein the active compound is N-(2,6-dichlorophenyl)-5-ethoxy-7-fluoro-1,2,4-triazolo-(1,5-c)pyrimidine-2-sulfonamide.

49. A composition as defined in claim 48 wherein the acid is phosphoric acid.

50. A composition as defined in claim 48 wherein the acid is monoammonium hydrogen phosphate.

51. A composition as defined in claim 29 wherein the active compound is N-(2-chloro-6-flourophenyl)- 5-ethoxy-7-fluoro-1,2,4-triazolo-(1,5-c)pyrimidine-2-sulfonamide.

52. A composition as defined in claim 51 wherein the acid is phosphoric acid.

53. A composition as defined in claim 51 wherein the acid is monoammonium hydrogen phosphate.

54. A composition as defined in claim 29 wherein the active compound is N-(2,6-difluorophenyl)-8-chloro-5-methoxy-1,2,4-triazolo-(1,5-c)pyrimidine-2-sulfonamide.

55. A composition as defined in claim 54 wherein the acid is phosphoric acid.

56. A composition as defined in claim 54 wherein the acid is monoammonium hydrogen phosphate.

57. A method for reducing the phytotoxicity toward grassy and broadleaf crop plants of sulfonamide and sulfonylurea herbicides employed in the post-emergent selective kill and control of broadleaf weeds growing in the presence of said grassy crop plants which comprises contacting said plants or their habitat with a herbicidally effective amount of an aqueous formulation containing, as the active material, a sulfonamide or sulfonylurea herbicide from the group consisting of
Chlorimuron-ethyl,
Chlorsulfuron,
Metsulfuron-methyl,
Tribenuron-methyl,
Thifensulfuron,
N-(2,6-dichloro-3-methylphenyl)-5,7-dimethoxy-1,2,4-triazolo(1,5-a)pyrimidine-2-sulfonamide,
N-(2,6-dichlorophenyl)-5-ethoxy-7-fluoro-1,2,4-triazolo-(1,5-c)pyrimidine-2-sulfonamide,
N-(2-chloro-6-fluorophenyl)-5-ethoxy-7-fluoro-1,2,4-triazolo-(1,5-c)pyrimidine-2-sulfonamide,
N-(2,6-difluorophenyl)-8-chloro 5-methoxy-1,2,4-triazolo-(1,5-c)pyrimidine-2-sulfonamide,
N-(2,6-difluorophenyl)-5-methyl-1,2,4-triazolo(1,5-a)pyrimidine-2-sulfonamide,
N-(2,6-difluorophenyl)-5-methoxy-8-fluoro-1,2,4-triazolo-(1,5-c)pyrimidine-2-sulfonamide, and
2-(((7-fluoro-5-ethoxy-1,2,4-triazolo(1,5-c)pyrimidin-2-yl) sulfonyl)amino)-3-fluorobenzoic acid, methyl ester,
or mixtures of said compounds, in admixture with water and an amount of a non-herbicidal acidic material from the group consisting of non-herbicidal organic or inorganic acids or the non-herbicidal acid salts of said inorganic acids or mixtures thereof sufficient to reduce the pH of said aqueous formulation to below about 5 and to provide in the final treating formulation from about 15 to about 1200 grams of acid equivalent per hectare.

58. A method as defined in claim 57 wherein the active compound is Chlorimuron-ethyl.

59. A method as defined in claim 58 wherein the acid is phosphoric acid.

60. A method as defined in claim 58 wherein the acid is monoammonium hydrogen phosphate.

61. A method as defined in claim 57 wherein the active compound is Chlorsulfuron.

62. A method as defined in claim 61 wherein the acid is phosphoric acid.

63. A method as defined in claim 61 wherein the acid is monoammonium hydrogen phosphate.

64. A method as defined in claim 57 wherein the active compound is Metsulfuron-methyl.

65. A method as defined in claim 64 wherein the acid is phosphoric acid.

66. A method as defined in claim 64 wherein the acid is monoammonium hydrogen phosphate.

67. A method as defined in claim 57 wherein the active compound is Tribenuron-methyl.

68. A method as defined in claim 67 wherein the acid is phosphoric acid.

69. A method as defined in claim 67 wherein the acid is monoammonium hydrogen phosphate.

70. A method as defined in claim 57 wherein the active compound is Thifensulfuron.

71. A method as defined in claim 70 wherein the acid is phosphoric acid.

72. A method as defined in claim 70 wherein the acid is monoammonium hydrogen phosphate.

73. A method as defined in claim 57 wherein the active compound is N-(2,6-dichloro-3-methylphenyl)- 5,7-dimethoxy-1,2,4-triazolo-(1,5-a)pyrimidine-2-sulfonamide.

74. A method as defined in claim 73 wherein the acid is phosphoric acid.

75. A method as defined in claim 73 wherein the acid is monoammonium hydrogen phosphate.

76. A method as defined in claim 57 wherein the active compound is N-(2,6-dichlorophenyl)-5-ethoxy-7-fluoro-1,2,4-triazolo-(1,5-c)pyrimidine-2-sulfonamide.

77. A method as defined in claim 76 wherein the acid is phosphoric acid.

78. A method as defined in claim 76 wherein the acid is monoammonium hydrogen phosphate.

79. A method as defined in claim 57 wherein the active compound is N-(2-chloro-6-flourophenyl)-5-ethoxy-7-fluoro-1,2,4-triazolo-(1,5-c)pyrimidine-2-sulfonamide.

80. A method as defined in claim 79 wherein the acid is phosphoric acid.

81. A method as defined in claim 79 wherein the acid is monoammonium hydrogen phosphate.

82. A method as defined in claim 57 wherein the active compound is N-(2,6-difluorophenyl)-8-chloro-5-methoxy-1,2,4-triazolo-(1,5-c)pyrimidine-2-sulfonamide.

83. A method as defined in claim 82 wherein the acid is phosphoric acid.

84. A method as defined in claim 82 wherein the acid is monoammonium hydrogen phosphate.

* * * * *